US00PP37366P2

(12) United States Plant Patent
Boxriker

(10) Patent No.: US PP37,366 P2
(45) Date of Patent: Apr. 14, 2026

(54) ***DIANTHUS* PLANT NAMED 'KLEDP23527'**

(50) Latin Name: ***Dianthus* x *caryophyllus* L. hort.**
Varietal Denomination: KLEDP23527

(71) Applicant: KLEMM + SOHN GMBH & CO. KG, Stuttgart (DE)

(72) Inventor: Maike Boxriker, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/226,675

(22) Filed: Jun. 3, 2025

(51) Int. Cl.
*A01H 5/02* (2018.01)
*A01H 6/30* (2018.01)

(52) U.S. Cl.
USPC ..... Plt./276

(58) Field of Classification Search
USPC ..... Plt./272, 273, 276
See application file for complete search history.

*Primary Examiner* — Susan McCormick Ewoldt
(74) *Attorney, Agent, or Firm* — Weatherly IP Solutions, LLC; John E. Pritchard; James Weatherly

(57) ABSTRACT

A new *Dianthus* plant designated 'KLEDP23527' particularly distinguished by pink flowers that transition from dark pink to light pink with the age of the flowers; and medium-sized, semi-upright, double flowers is disclosed.

2 Drawing Sheets

Genus and species: *Dianthus* x *caryophyllus* L. hort.
Variety denomination: 'KLEDP23527'.

BACKGROUND OF THE NEW PLANT

The present invention comprises a new and distinct variety of *Dianthus*, botanically known as *Dianthus* x *caryophyllus* L. hort. and hereinafter referred to by the variety name 'KLEDP23527'. 'KLEDP23527' originated from a whole plant mutation in a group of *Dianthus* 'DCP-2016-Sissy02' (unpatented) plants and discovered in a trial conducted between December 2017 and January 2018 in Stuttgart, Germany.

In June 2018 'KLEDP23527' was first vegetatively propagated by vegetative stem cuttings in Stuttgart, Germany. 'KLEDP23527' was found to reproduce true to type in successive generations of asexual propagation in Stuttgart, Germany via vegetative cuttings.

SUMMARY

The following are the most outstanding and distinguishing characteristics of 'KLEDP23527' when grown under normal horticultural practices in Stuttgart, Germany.

1. Pink flowers that transition from dark pink to light pink with age of the flowers; and
2. A medium-sized, semi-upright, double flower.

DESCRIPTION OF THE PHOTOGRAPHS

This new *Dianthus* plant is illustrated by the accompanying photographs. The colors shown are as true as can be reasonably obtained by conventional photographic procedures.

DESCRIPTION

Figure 1:
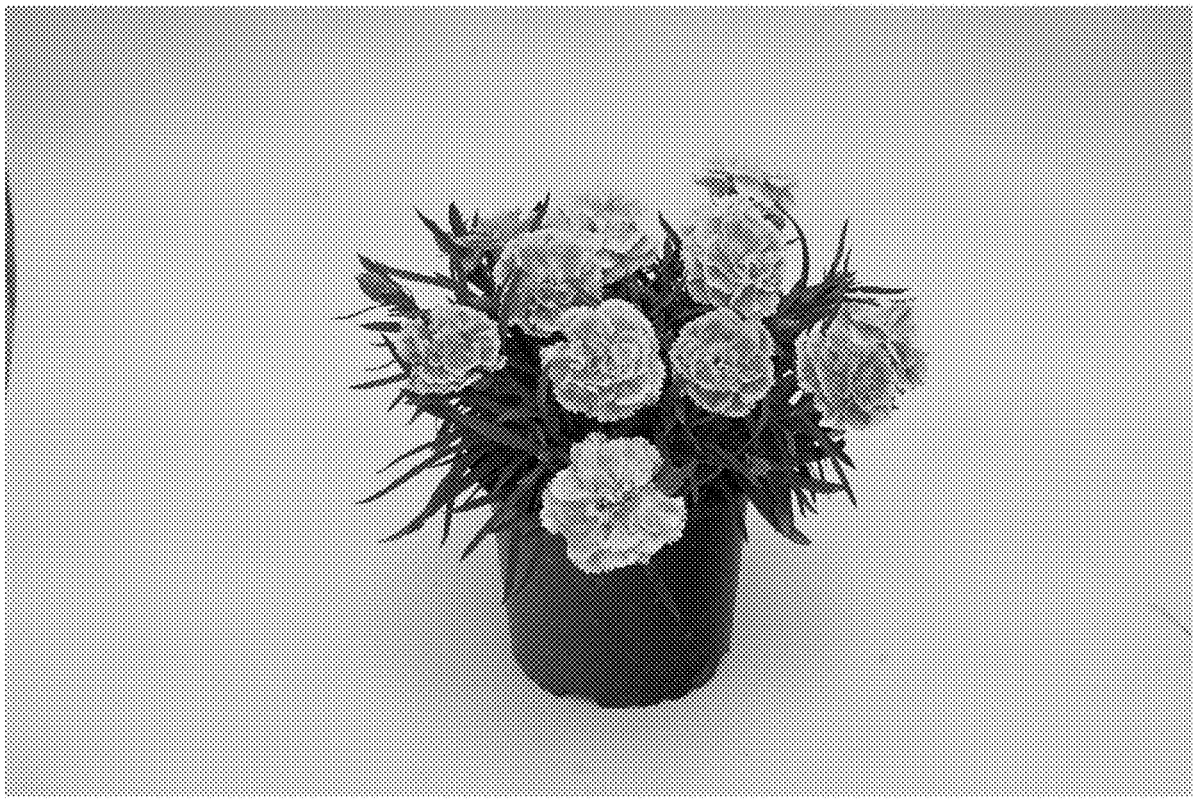
FIG. 1 is a photograph showing a whole plant of 'KLEDP23527' at 13-weeks old in March 2023 in Stuttgart, Germany and shows the foliage, buds, and flowers.
Figure 2:
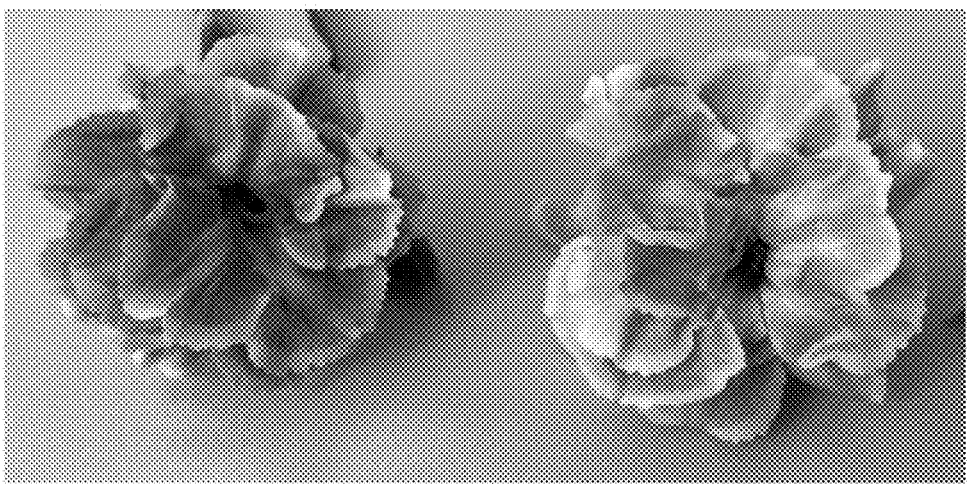
FIG. 2 shows a comparison of a young flower of 'KLEDP23527' with a dark pink color next to an older flower with a light pink color.

The following detailed descriptions set forth the distinctive characteristics of 'KLEDP23527'. The data which define these characteristics were collected from asexual reproductions carried out in Stuttgart, Germany. Data was collected in April 2025 from a plant that had been potted in week 37 of 2024 and grown in a greenhouse in Stuttgart, Germany. Color references are to The R.H.S. Colour Chart of The Royal Horticultural Society of London (R.H.S.), 5$^{th}$ edition (2007).

Classification:
- *Family.*—Caryophyllaceae.
- *Botanical.*—*Dianthus caryophyllus* L. hort.
- *Designation.*—'KLEDP23527'.
- *Type.*—Pot carnation.

Parentage: Whole plant mutation discovered in a group of *Dianthus* 'DCP-2016-Sissy02' (unpatented) plants.

Plant:
- *Propagation type.*—Vegetative cuttings.
- *Time to produce a rooted young plant.*—28 days.
- *Root description.*—Fine, color RHS 155C.
- *Rooting habit shape.*—Lanceolate.
- *Plant form.*—Semi-upright.
- *Plant height.*—16 cm.
- *Plant diameter or spread.*—26 cm.

Lateral branches/stems:
- *Shape of the branch in cross-section.*—Circular.
- *Hollowness of the branch.*—Absent.
- *Length.*—17 cm.
- *Diameter.*—2.5 cm.
- *Internode length.*—4.5 cm.
- *Internode quantity per branch.*—4.
- *Number of internodes per branch/stem.*—4.
- *Node length.*—0.3 cm.
- *Node diameter.*—0.4 cm.
- *Texture.*—Smooth.
- *Color.*—N137A.
- *Flower clustering on the lateral branch.*—On some lateral branches.

Foliage:

*Arrangement*.—Opposite.
*Length*.—4.5 cm.
*Width*.—0.3 cm.
*Shape*.—Linear.
*Apex*.—Acute.
*Base*.—Obtuse.
*Margin*.—Entire.
*Texture* (*both upper and lower surfaces*).—Smooth.
*Cross-section of the leaf*.—Moderately concave.
*Curvature of the leaf*.—Absent.
*Glaucosity of the leaf*.—Weak.
*Leaf color* (*both immature and mature*).—Immature: Upper surface: 137A. Lower surface: N137A. Mature: Upper surface: N137A. Lower surface: N137A.
*Venation pattern*.—Absent.

Flowers:

*Flower type and habit*.—Double sprays.
*Fragrance*.—Present.
*Position of the flowers compared to the foliage of the plant*.—Moderately above.
*Profile of both the upper and lower part in the lateral view*.—Flat convex.
*Diameter of the flower*.—4.7 cm.
*Natural flowering season*.—Spring to autumn.
*Number of flowers per spray*.—3 to 4.
*Flower longevity on the plant*.—12 days.

Buds:

*Length*.—2.0 cm.
*Diameter*.—0.9 cm.
*Shape*.—Oblong.
*Color*.—137A.
*Extrusion of the styles at the bud stage*.—Absent.

Corolla:

*Quantity of petals and arrangement*.—15 and arranged in several whorls.
*Corolla height*.—2.0 cm.
*Petal length*.—3.5 cm.
*Petal width*.—1.9 cm.
*Petal shape*.—Obtuse.
*Petal apex*.—Obtuse.
*Petal base*.—Acute.
*Petal margin*.—Crenate.
*Depth of petal margin*.—Medium.
*Petal texture* (*both upper and lower surfaces*).—Smooth.
*Petal color*.—Immature: Upper surface: N66C with 65B margin. Lower surface: 69D. Mature: Upper surface: 68D with 69C margin. Lower surface: 69D.
*Macule*.—Absent.

Calyx:

*Quantity of sepals and arrangement*.—5. Longitudinal axis of the lobes of the calyx: Straight. Shape: Campanulate. Calyx height: 2.1 cm. Calyx diameter (at the apex): 0.7 cm. Sepal texture (both upper and lower surfaces): Smooth. Sepal color: Upper surface: 137B. Lower surface: 144A.
*Position of the outer lobes of the epicalyx in relation to the calyx*.—Adpressed.
*Apex shape of the outer lobes of the epicalyx*.—Short acuminate.
*Tip length of the outer lobes of the epicalyx*.—0.1 cm.
*Apex shape of the inner lobes of the epicalyx*.—Short acuminate.
*Tip length of the inner lobes of the epicalyx*.—0.1 cm.

Peduncles:

*Length*.—2.8 cm.
*Diameter*.—0.2 cm.
*Strength*.—Medium.
*Texture*.—Smooth.
*Color*.—N137A.

Reproductive organs:

*Stamens*.—Quantity per flower: 6. Filament length: 1.3 cm. Filament color: 160B. Anther length: 0.2 cm. Anther diameter: 0.1 cm. Anther color: 164B. Pollen amount: None observed.
*Pistils*.—Quantity per flower: 2. Length: 1.7 cm. Diameter: 0.1 cm. Stigma: Color: 73A. Shape: Filamentous. Length: 0.3 cm. Diameter: 0.1 cm.
*Style*.—Color: 157A. Length: 1.4 cm. Diameter: 0.1 cm.
*Ovary*.—Color: 145C. Width: 0.5 cm.

Seeds: None observed to date.

Disease and insect resistance: No particular disease or insect resistance observed.

COMPARISON OF 'KLEDP23527' WITH PARENTAL LINE AND KNOWN VARIETY

'KLEDP23527' is distinguished from the parent as described in Table 1.

TABLE 1

Comparison with Parental Line

| Characteristic | 'KLEDP23527' | Female parent |
|---|---|---|
| Flower color | Younger flowers are dark pink that transition to light pink with age | Purple |

'KLEDP23527' can be compared to the commercial *Dianthus* variety 'KLEDP07089' (unpatented). Differences between the varieties are described in Table 2.

TABLE 2

Comparison with Similar Variety

| Characteristic | 'KLEDP23527' | 'KLEDP07089' (unpatented) |
|---|---|---|
| Habit | Semi-upright | Upright |
| Flower | Double | Semi-double |
| Flower size | Smaller than 'KLEDP07089' | Larger than 'KLEDP23527' |

I claim:

1. A new and distinct variety of *Dianthus* plant designated 'KLEDP23527' as illustrated and described herein.

* * * * *